United States Patent
Guarino et al.

(10) Patent No.: US 11,067,555 B2
(45) Date of Patent: Jul. 20, 2021

(54) SYSTEM AND METHOD FOR DETECTING ENTERIC DISEASES, IN PARTICULAR IN ANIMALS, BASED ON ODOUR EMISSIONS

(71) Applicant: UNIVERSITA' DEGLI STUDI DI MILANO, Milan (IT)

(72) Inventors: Marcella Guarino, Milan (IT); Valentina Ferrante, Vignate (IT); Guido Grilli, Alessandria (IT); Federica Borgonovo, Milan (IT); Lorenzo Ferrari, Gaggiano (IT); Andrea Giovanni Pastori, Brugherio (IT); Ilaria Fontana, Sesto Calende (IT); Emanuela Tullo, Pioltello (IT); Paolo Guffanti, Lodi (IT)

(73) Assignee: UNIVERSITA' DEGLI STUDI DI MILANO, Milan (IT)

( * ) Notice: Subject to any disclaimer, the term of this patent is extended or adjusted under 35 U.S.C. 154(b) by 100 days.

(21) Appl. No.: 16/308,195

(22) PCT Filed: Jun. 8, 2017

(86) PCT No.: PCT/IB2017/053397
§ 371 (c)(1),
(2) Date: Dec. 7, 2018

(87) PCT Pub. No.: WO2017/212437
PCT Pub. Date: Dec. 14, 2017

(65) Prior Publication Data
US 2019/0302074 A1    Oct. 3, 2019

(30) Foreign Application Priority Data
Jun. 9, 2016    (IT) .................... 102016000059153

(51) Int. Cl.
*G01N 33/00* (2006.01)
*A61B 5/00* (2006.01)
(Continued)

(52) U.S. Cl.
CPC ....... *G01N 33/0031* (2013.01); *A61B 5/4255* (2013.01); *A61B 5/7275* (2013.01);
(Continued)

(58) Field of Classification Search
CPC .... G01N 27/12; G01N 27/414; G01N 33/005; G01N 33/004; G01N 27/122;
(Continued)

(56) References Cited

U.S. PATENT DOCUMENTS 5,571,401 A * 11/1996 Lewis .................. G01N 27/126
205/787
5,788,833 A * 8/1998 Lewis ................ G01N 33/0031
204/406
(Continued)

FOREIGN PATENT DOCUMENTS

WO    WO-9708337 A1 *    3/1997    ........... G01N 33/497
WO    WO-02086149 A2 * 10/2002    ............. G01N 33/84
WO    WO-2017212437 A1 * 12/2017    ............. A61B 5/746

OTHER PUBLICATIONS

Van Harreveld et al., 'Progresss of EN13725 revision the standard used to determine odour concentration and odour treatment efficiency', Abstract, 2003 6 pages (Year: 2003).*
(Continued)

*Primary Examiner* — Clayton E. LaBalle
*Assistant Examiner* — Kevin C Butler
(74) *Attorney, Agent, or Firm* — Merchant & Gould P.C.

(57) ABSTRACT

A detection system (101, 101b) of enteric diseases in animals includes a sensor device (102) having suction (103) for suctioning air from the animals' environment (11, 12). A
(Continued)

sensor is (104) configured to determine information about the type and concentration of smelling molecules in the air and further configured to emit a signal representative of the information of smelling molecules. A transmission device (105) is configured to convey the signal representative of smelling molecules. A self-learning processing device (108) is configured to receive and process the signal representative of smelling molecules, and to detect a risk of enteric diseases in the animals associated with the information about the type and concentration of the smelling molecules. A signaling device (111) is configured to report to a user (10) the risk of enteric diseases in the animals, before the enteric diseases arise. A relative method detects enteric diseases in animals.

15 Claims, 4 Drawing Sheets

(51) Int. Cl.
  *A61B 10/00* (2006.01)
  *G01N 27/12* (2006.01)
  *G01N 27/414* (2006.01)
(52) U.S. Cl.
  CPC .............. *A61B 5/746* (2013.01); *A61B 10/00* (2013.01); *G01N 27/12* (2013.01); *G01N 27/122* (2013.01); *G01N 27/414* (2013.01); *G01N 33/004* (2013.01); *G01N 33/005* (2013.01); *G01N 33/0047* (2013.01); *A61B 2010/0087* (2013.01); *A61B 2503/40* (2013.01); *G01N 2800/06* (2013.01)
(58) Field of Classification Search
  CPC .............. G01N 33/0031; A61B 5/4255; A61B 5/7275; A61B 5/746; A61B 10/00
  USPC ........................................................ 73/31.06
  See application file for complete search history.

(56) References Cited

U.S. PATENT DOCUMENTS

| | | | | |
|---|---|---|---|---|
| 5,807,701 | A * | 9/1998 | Payne | C12Q 1/04 422/50 |
| 5,928,609 | A * | 7/1999 | Gibson | G01N 33/0031 422/90 |
| 6,244,096 | B1 * | 6/2001 | Lewis | A61B 5/00 422/78 |
| 6,305,214 | B1 * | 10/2001 | Schattke | G01N 27/4045 204/412 |
| 6,387,329 | B1 * | 5/2002 | Lewis | G01N 15/0826 422/83 |
| 6,408,250 | B1 * | 6/2002 | Grate | B82Y 30/00 702/22 |
| 6,461,306 | B1 * | 10/2002 | Hanson | A61B 5/7264 600/532 |
| 6,571,603 | B1 * | 6/2003 | Doleman | G01N 33/0031 702/19 |
| 6,631,333 | B1 * | 10/2003 | Lewis | G01N 33/0031 702/23 |
| 6,844,197 | B1 * | 1/2005 | Doleman | G01N 33/0006 422/82.01 |
| 6,895,338 | B2 * | 5/2005 | Hsiung | G01N 33/0031 422/82.01 |
| 7,255,677 | B2 * | 8/2007 | Burch | A61B 5/00 600/300 |
| 9,448,180 | B2 * | 9/2016 | O'Dell | G01N 33/0057 |
| 9,651,529 | B2 * | 5/2017 | Hamidon | G01N 33/0031 |
| 2002/0005580 | A1 * | 1/2002 | Goodman | G01N 33/0031 257/734 |
| 2003/0136960 | A1 * | 7/2003 | Goodman | G01N 27/128 257/40 |
| 2019/0302074 | A1 * | 10/2019 | Guarino | A61B 5/746 |

OTHER PUBLICATIONS

Laura Capelli et al., 'Odor Sampling: Techniques and Strategies for the Estimation of Odor Emission Rates from Different Source Types', Jan. 15, 2013, 18 pages (Year: 2013).*
Prof. Dr.-Ing. Franz-Bernd Frechen, State of the Art of Odour Measurement, Dept. of Sanitary and Environmental Engineering, 149-155 pages (Year: 2003).*
Alphus Dan Wilson, Applications of Electronic-Nose Technologies for Noninvasive Early Detection of Plant, Animal and Human Diseases, Chemosensors 2018, 6, 45; doi:10.3390/chemosensors6040045, 2018, 37 pages (Year: 2018).*
Ministry of the Enviroment, Odor Measurement, https://www.env.go.jp/en/air/odor/measure/, 2017, 2 pages (Year: 2017).*
Peled Nir et al, 'Detection of volatile organic compounds in cattle naturally infected with *Mycobacterium bovis*', Sensors and Actuators B 171-172 (2012) 588-594 (Year: 2012).*
Pavlou A.K. et al, 'Sniffing out the truth: clinical Diagnosis using the electronic nose', Clin Chem Lab Med 2000; 38(2):99-112 (Year: 2000).*
International Search Report and Written Opinion of the International Searching Authority for International Patent Application No. PCT/1132017/053397 dated Aug. 30, 2017, 13 pages.
Anonymous: "Veterinary Advice Online—Coccidia Infection. Coccidiosis in dogs and cats and other animals", XP055337646, retrieved from the Internet: http://www.pet-informed-veterinary-advice-online.com/coccidiosis-in-dogs.html [retrieved on Jan. 23, 2017], 70 pages (May 2008).
Elliot-Martin, R. et al., "Preliminary Investigation of Breath Sampling as a Monitor of Health in Dairy Cattle", Journal of Agriculture Engineering Research, 67(4): 267-275 (Aug. 1997).
Fend, R. et al., "Use of an electronic nose to diagnose Mycobacterium bovis infection in badgers and cattle", Journal of Clinical Microbiology, American Society for Microbiology, 43(4): 1745-1751 (Apr. 2005).
Johnson, R. et al., "MEMS-Enabled Electronic Nose is Nothing to Sneeze At EE Times", XP055337746, retrieved from the Internet: http://www.eetimes.com/document.asp?doc [retrieved on Jan. 23, 2017], 4 pages (Aug. 2013).
Kadesh, A., "Sniffing out disease", XP055337631, retrieved from Internet: http://webcache.googleusercontent.com/serach?q=cache:FFqjjwEaD0wJ:mfa.gov.il/MFA/Innovativelsrael/Pages/Sniffing_disease-May_2011.aspx+&dc 1-108,h1=en&ct=clnk&gl=nl[retrieved on 23 Jan. 2017], 4 pages (Sep. 2011).
Probert, C. et al., "A novel method for rapidly diagnosing the causes of diarrhoea", GUT, 53(1): 58-61 (Jan. 2004).
Sesam, et al., "Vovinose Report Summary", XP055337726, retrieved from the Internet: http://cordis.europa.eu/ result/rcn/58187_en.pdf [retrieved on Jan. 23, 2017], 19 pages (Jun. 2013).
Turner, A. et al., "Electronic noses and disease diagnostics", Nature Reviews, Microbiology, Nature Publishing Group, 2(2): 161-165 (Feb. 2004).
Wilson, A et al., "Advances in Electronic-Nose Technologies Developed for Biomedical Applications", Sensors, 11(12): 1105-1176 (Dec. 2011).

* cited by examiner

SYSTEM AND METHOD FOR DETECTING ENTERIC DISEASES, IN PARTICULAR IN ANIMALS, BASED ON ODOUR EMISSIONS

This application is a National Stage Application of PCT/IB2017/053397, filed 8 Jun. 2017, which claims the benefit of Serial No. 102016000059153, filed 9 Jun. 2016 in Italy, and which applications are incorporated herein by reference. To the extent appropriate, a claim of priority is made to each of the above-disclosed applications.

FIELD OF THE INVENTION

The present invention relates to detection system of enteric diseases, in particular in animals, and to a relating detection method of enteric diseases, in particular in animals. In general, the present invention relates to detection systems of diseases in animals, in particular in farm animals, aimed at monitoring the health of the population.

PRIOR ART

Enteric diseases are present in all species of zootechnical interest (e.g. poultry, rabbits, pigs, cattle and sheeps and goats); at present, if there are no specific vaccines, they are only diagnosed at the onset of clinical symptoms (usually diarrhea) and then treated with antibiotics or pesticides.

An example of enteric disease is coccidiosis, which is a parasitic disease caused by the development and multiplication of protozoa called coccidia, obligate parasites that colonize the intestine epithelial cells. Coccidiosis, in sub clinical form, can cause the reduction of the production performance without obvious symptoms, while in the cases of full-blown pathology it can cause hemorrhagic diarrhea, up to the death of a large number of subjects if nothing is done in a timely manner.

From an economic point of view, the damage caused by coccidiosis cause heavy losses both in breeding of commercial birds (broilers, turkeys, hens) and in all other species of zootechnical interest where coccidiosis has a relevant health impact.

Currently, the prophylaxis and treatment of coccidiosis are implemented with:
1) vaccines: expensive, not readily applicable and not always available for all animal species.
2) molecules with coccidiostatic and anti-coccidiosis action: administered in food throughout the cycle as it normally occurs in broilers and rabbits, with the exception of the pre-slaughter withdrawal period of 7 days. This usage involves the continuous administration of molecules that, if not properly alternated, can induce resistance in coccidia, in addition to having high costs and the need for dedicated silos.
3) Short term therapies may be needed in cases of sub-clinical/clinical coccidiosis in farms where prophylaxis has not been effective. In these cases, the withdrawal period from the drug can delay the slaughter of the animal, with additional cost and production inconvenience. In laying hen breeding, however, anti-coccidiosis drugs cannot be administered; for this reason, the prevention and control of coccidiosis must be applied in the pullet chain.

The only currently possible early diagnosis of coccidiosis involves a periodic count of oocysts in faeces and/or the euthanization of some subjects to assess the presence of coccidia in several sections of the intestine, removed from the animal. This method exhibits problems both from a practical point of view, because the method is within the reach of only a few laboratories, and as regards ethics.

The methods of detection of intestinal infections are varied and not always effective, especially for an early diagnosis of intestinal diseases.

OBJECTS AND SUMMARY OF THE INVENTION

The object of the present invention is to provide a system for the early diagnosis of enteric diseases and a relating detection method of enteric diseases that solve some drawbacks of the prior art.

In particular, the object of the present invention is to propose a system and method of detection of enteric diseases in animals that will effectively control the onset of diseases, in particular for optimizing the profitability of livestock farms.

Another object of the present invention is to propose a system and method of detection of enteric diseases in animals that allow early detection of the onset of enteric diseases, especially in livestock.

It is therefore an object of the present invention to propose a system and method of detection of enteric diseases in animals, which are practical and fast for the user who carries out detection, being desirable from an operational point of view.

These and other objects of the present invention are achieved by a detection system of enteric diseases in animals, and a relating method, incorporating the features of the appended claims which form an integral part of the present description.

A general idea underlying the present invention is to provide a detection system of enteric diseases in animals, comprising: a sensor device comprising suction means for suctioning air from an environment where the animals are and sensor means configured to determine information about the type and concentration of a plurality of smelling molecules in the air and further configured to emit a signal representative of the information of smelling molecules; a transmission device configured to convey the signal representative of the smelling molecules; a processing device configured to receive and process the signal representative of smelling molecules, detecting a risk of enteric diseases in the animals associated with the information about the type and concentration of smelling molecules; a signaling device configured to report to a user the risk of enteric diseases in the animals.

A further general idea underlying the present invention is to provide a detection method of enteric diseases in animals, comprising: suctioning air from an environment with animals therein; determining by means of sensor means information about the type and concentration of a plurality of smelling molecules in the air; detecting a risk of enteric diseases in the animals associated with the information about the type and concentration of smelling molecules; reporting to a user the risk of enteric diseases in the animals.

In general, a system according to the present invention is adapted to implement the detection method of enteric diseases in animals.

In general, the system and method according to the present invention allow detecting the onset of enteric diseases, particularly in livestock, reducing economic losses for breeders. In fact, the device detects a unique mark of the smell corresponding to the onset of an enteric disease (for example, coccidia and other intestinal tropism pathogens, particularly in breeding bird species and other livestock, such as mammals).

In addition, the system and method according to the present invention allow an early detection of the onset of enteric diseases, especially in livestock, constituting therefore an "early warning" for the breeder.

In addition, the system and method according to the present invention are practical and fast for the breeder, both from an operating and a practical point of view.

This system is particularly advantageous in farms with a large number of heads.

Further objects and advantages of the present invention will appear clearly from the following detailed description of some embodiments examples, made by way of non-limiting explanation.

BRIEF DESCRIPTION OF THE DRAWINGS

These embodiments are described with reference to the accompanying drawings, also provided purely by way of non-limiting example, in which.

Where appropriate, similar or identical elements in different figures are indicated by the same or similar reference numerals.

DETAILED DESCRIPTION OF THE INVENTION

Figure 1:
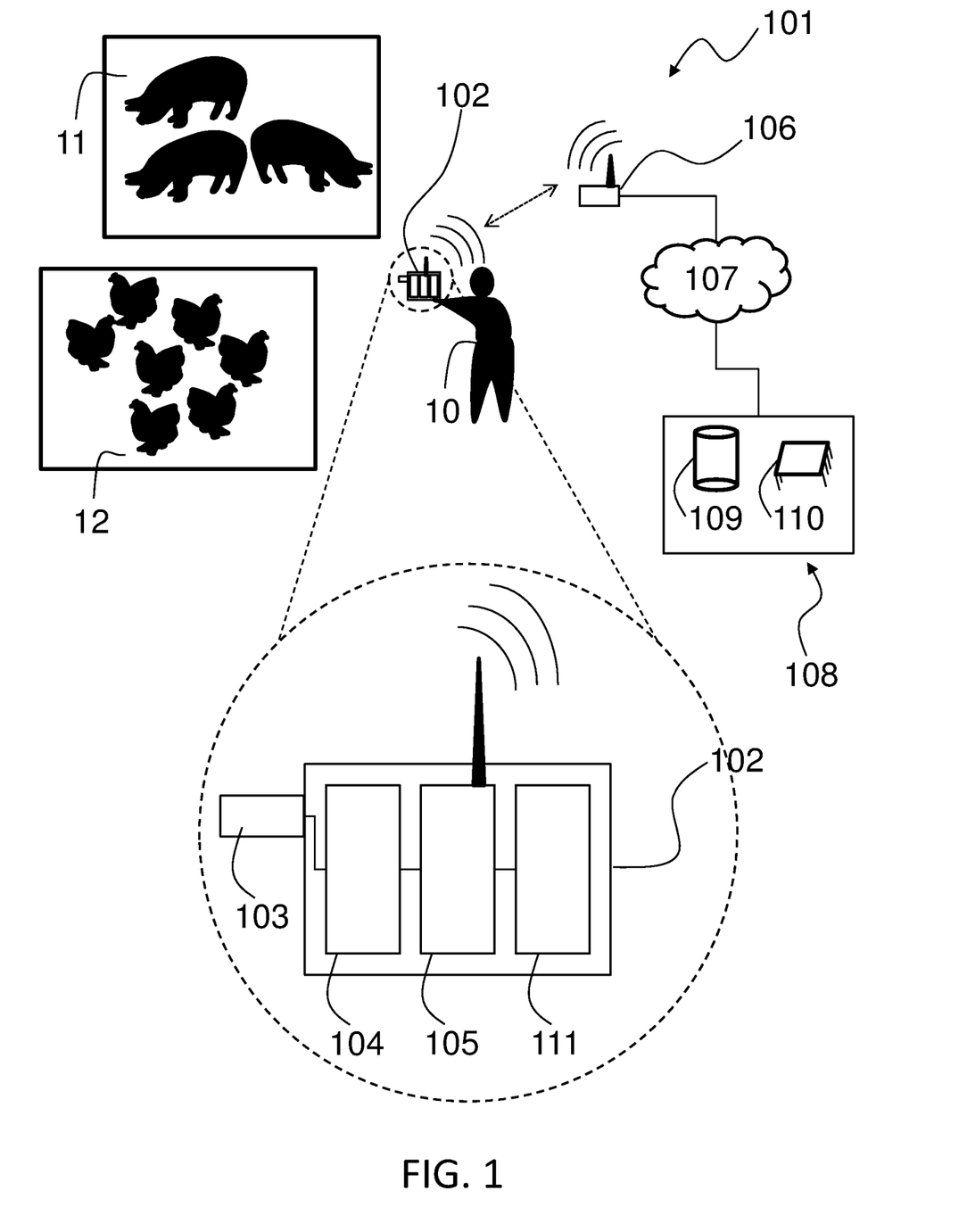
FIG. 1 shows a first embodiment of a detection system of enteric diseases in animals according to the present invention.

The example in FIG. 1 shows a first embodiment of a detection system 101 of enteric diseases in animals according to the present invention.

The detection system 101 comprises a sensor device 102, operable by a user 10 who goes to inspect an environment with animals, such as environment 11 (a stable for pigs) or environment 12 (a chicken coop).

The sensor device 102 comprises suction means 103, such as a plunger, a spout, a fan etc., which are adapted to suction air from environment 11 or 12 for subsequent analysis.

The sensor device 102 further comprises sensor means 104, which are configured to determine information about the type and concentration of a plurality of smelling molecules in the suctioned air and emit a signal representative of the information about the smelling molecules present in such air.

Preferably, the sensor means 104 comprise a plurality of sensors (not shown), each being adapted to analyze at least a respective type of smelling molecule. Preferably, such sensors are MOS sensors for gases, preferably comprising at least three sensors, and more preferably comprising five or more sensors.

In general, the sensor device 102 corresponds to a device called "electronic nose".

In fact, in response to the growing demand for objective sensory analysis, instruments have been developed which are capable of measuring, characterizing and transforming subjective information into objective and measurable data, starting from the volatile aromas. The "electronic nose" is a device which, using different non-specific chemical sensors, does not recognize the different substances individually, but identifies and creates an olfactory mark (using a pattern recognition system) of the mixture analyzed. These sensors are able to alter their electrical characteristics in the presence of the different volatile compounds, thereby providing a diversified electrical signal in response to the concentration of the different classes of volatile compounds present in the mixture. The sensors of the electronic nose can be classified into hot sensors (Metal Oxide Semiconductors—MOS—and Metal Oxide Semiconductor Field Effect Transitor—MOSFET) and cold sensors (Conductive polymers—CP—and Quartz Crystal Microbalance—QCM). The electronic nose can emulate the human olfactory system, providing a unique mark of a particular smell, allowing the subsequent recognition thereof.

In particular, MOS (Metal Oxide Semiconductor) sensors consist of three layers: ceramic substrate, heating wire, metal oxide semiconductor film.

The principle of operation of MOS sensor is based on conductivity changes induced by superficial reactions due to the adsorption of the gas analyzed. Due to the different temperatures (150 to 500° C.) at which the sensors work, they are sensitive to various gases. The change in resistance recorded and correlated to the adsorbed compounds is caused by the exchange of oxygen between the volatile molecules and the metal oxide film.

The sensor device 102 in particular comprises at least three sensors, and more in particular five or more sensors, selected from any of the following adapted to identify: Toluene, $NO_2$, Benzene, $H_2$, Propane, $CH_4$, CO, $H_2S$ and aromatic, $CH_4$ at a high concentration. In particular, the sensors that are more sensitive to the molecules present in the ambient air of livestock farms are those for nitrogen oxides, $CH_4$ and light hydrocarbons, sulfur compounds, CO and aromatic.

As mentioned, the sensor device 102 is adapted to emit a signal representative of information about the smelling molecules present in the air analyzed.

The detection system 101 further comprises a transmission device 105 configured to convey the signal representative of smelling molecules and transmit it.

Preferably, the transmission device 105 is configured to provide a bi-directional data exchange connection. In the example in FIG. 1, the transmission device 105 is a WiFi module configured to connect to the Internet network 107 through the Access Point 106.

In addition, the detection system 101 comprises a processing device 108 configured to receive and process the signal representative of the smelling molecules, detecting a risk of enteric diseases in the animals. The risk of enteric disease is in fact associated with the information detected about the type and concentration of the smelling molecules, as will be explained in more detail hereinafter.

Preferably, the processing device 108 further comprises a memory 109, in which reference data relating to the type and concentration of smelling molecules, in enteric disease cases in animals are stored. Memory 109 is operatively associated with a processor 110 of the processing device 108, so as to compare the information gathered by the sensor device 102 about the type and concentration of said smelling molecules with the reference data stored.

In particular, processor 110 is adapted to differentiate the risk of enteric diseases in animals by comparing a concentration of at least one or preferably several types of smelling molecules with respect to the reference values in the reference data stored.

In a preferred embodiment, the detection system 110, preferably using hot MOS sensors of the sensor device 102, is therefore able to provide a unique mark of the enteric disease that occurs in the animal population monitored. Due to the high sensitivity of the sensor device 102, the onset of the enteric disease can be identified before it becomes apparent within a larger breeding group. Hence the value of the detection system 101 as an early warning able to intervene early to contain the spread of the disease. In this way, it is thought to significantly reduce the use of antibiotics in livestock, thus improving the healthiness of meat for consumers, reducing the environmental impact, costs and reducing the phenomenon of antibiotic resistance.

Preferably, the processing device 108 is further adapted to store information transmitted thereto about the type and concentration of said smelling molecules by associating them with the reference data for subsequent analysis. In this way, a statistical basis for enteric disease risk data can be populated, thus improving the reliability of the detection method.

In other words, the detection system 101 can record values previously read and store them, so as to build a set of increasingly precise reference data to correctly classify the subsequent detections. Then, the detection system 101 is able to implement a form of self-learning (capacity of an electronic device to change its behavior according to the impulses it receives from the outside) and improve itself, as will be explained in more detail hereinafter.

Finally, the detection system 101 further comprises a signaling device 111, configured to alert the user 10 of the risk of enteric diseases in animals 11 or 12. In a preferred embodiment, this signaling device comprises a display positioned on the sensor device 102. Preferably, such display provides a synthetic indication, such as a "traffic light" with three levels depending on the risk of existence of enteric disease in the population, or other display modes.

Preferably, the sensor device 102 can be updated with new data and functions through the Internet connection 106 and 107.

Figure 2:
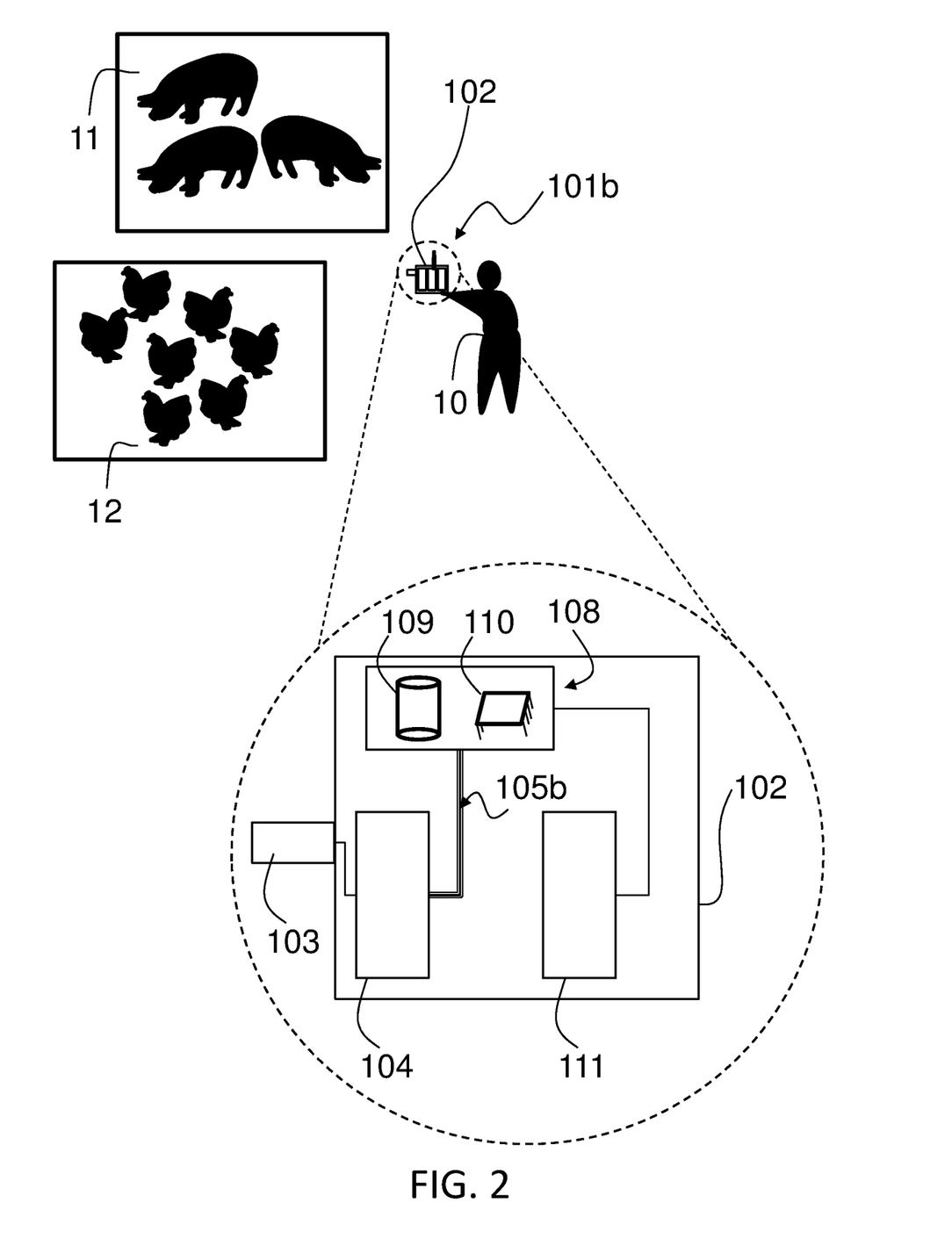
FIG. 2 shows a second embodiment of a detection system of enteric diseases in animals according to the present invention.

The example in FIG. 2 shows a second embodiment of a detection system 101b of enteric diseases in animals according to the present invention.

The detection system 101b comprises all the elements of the system described above, replacing the wireless connection of the transmission device with a wired connection 105b. In this sense, the detection system 101b consists of an all in one independent embodiment adapted to operate also without Internet connections. The embodiment of the detection system 101b, while being more practical, is more expensive as it requires a dedicated processing device 108.

Figure 3:
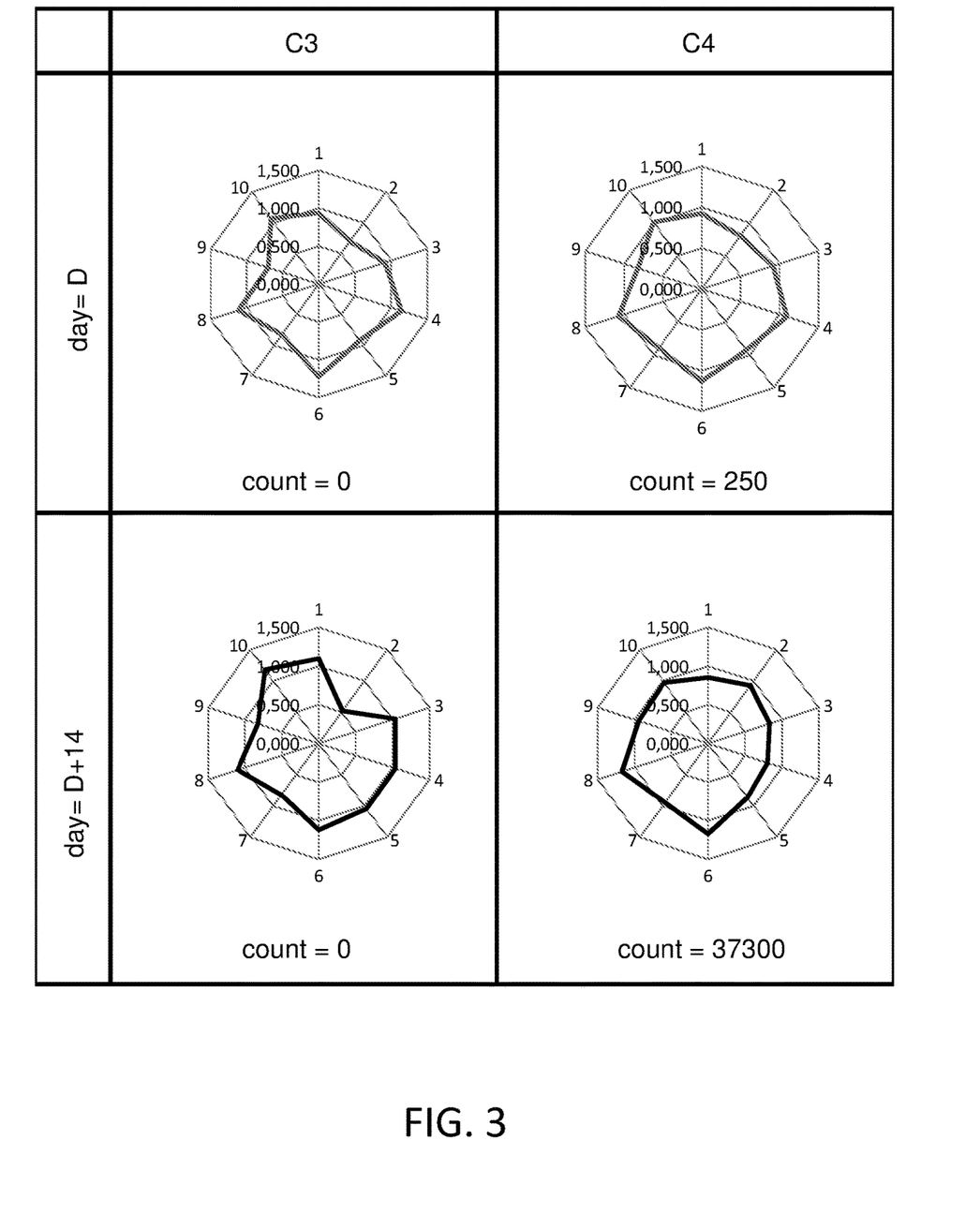
FIG. 3 shows an exemplification graph of experimental data in relation to the detection method of enteric diseases in animals according to the present invention.
Figure 4:
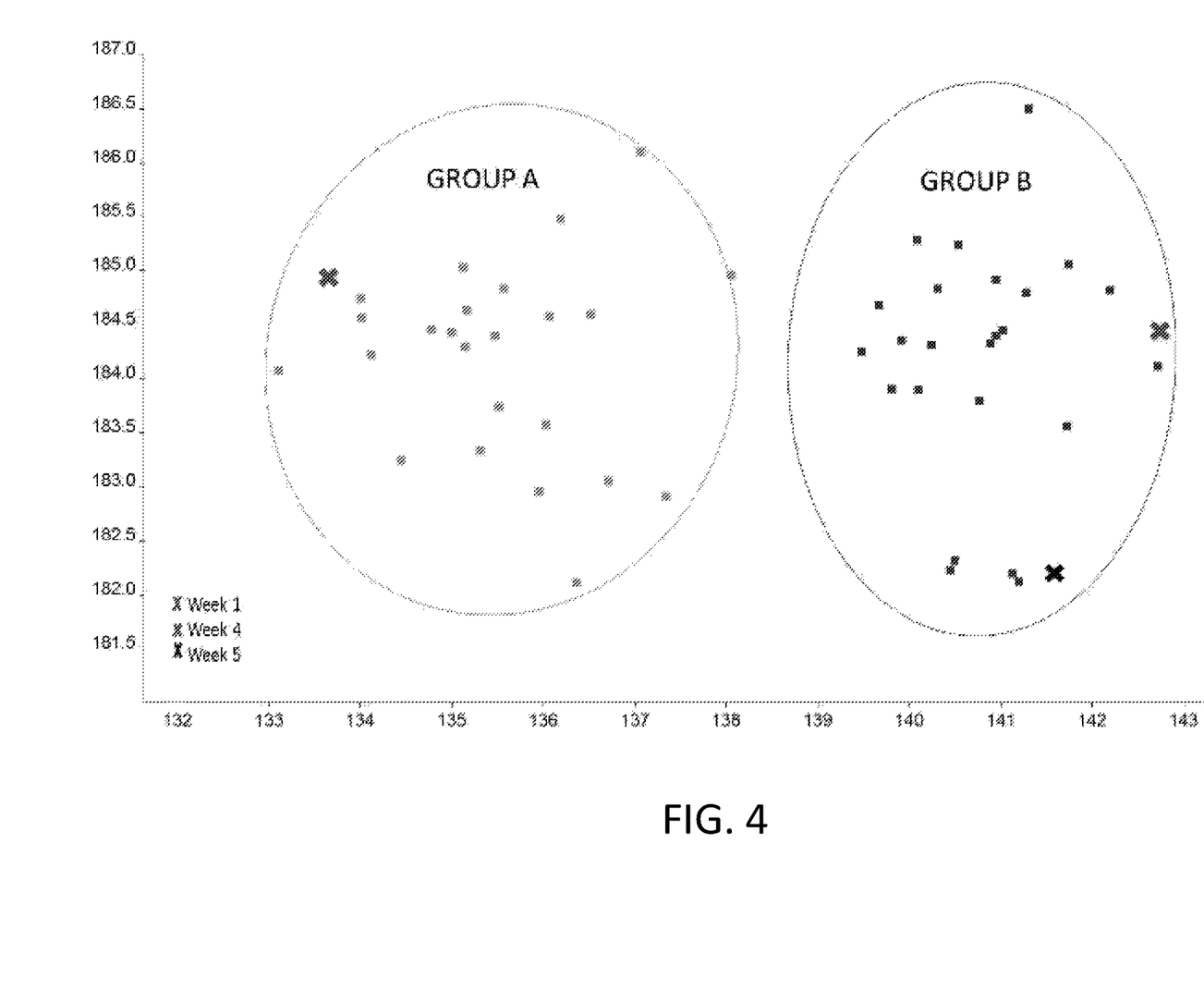
FIG. 4 shows a second exemplification graph of experimental data in relation to the detection method of enteric diseases in animals according to the present invention, obtained with linear discriminant analysis (LDA).

In relation inter alia to FIG. 3 and FIG. 4, experimental data obtained by a detection method of enteric diseases in animals according to the present invention are now exemplified.

The detection method of enteric diseases in animals provides for suctioning air from an environment with said animals; determining by means of sensor means information about the type and concentration of a plurality of smelling molecules in the air; detecting a risk of enteric diseases associated with the information about the type and concentration of smelling molecules; reporting to a user a risk of enteric diseases in the animals.

In particular, the information about the type and concentration of the smelling molecules are compared with reference data stored and referred to enteric disease cases in animals, preferably by differentiating enteric diseases in animals by comparing a concentration of at least one or preferably several types of smelling molecules with respect to reference values of the reference data. Following the aforementioned ability of self-learning of the system, the dataset becomes increasingly reliable in properly classifying the samples in the infected and uninfected category.

The detecting system transmits to the processing device, at predefined times, the detections of the sensors in the form of electrical signal (resistance) in ohms. These measures are analyzed through a PCA model that, explaining the variance thereof, places them in two different areas of the multivariate space created. Such positions (see FIG. 4) represent the uninfected and the infected animals according to a conventional diagnostic reference system (gold standard). The multivariate space in both situations is compacted, becoming increasingly defined as data arrives to the server, thus making the analysis increasingly targeted and accurate for the pathology and breeding (self-learning).

The system allows an early warning on enteric diseases; in fact, the system is able to detect changes in smell as soon as they occur and long before the possibility of a clinical diagnosis, and thus before the enteric diseases arise.

In the embodiment of the detection method exemplified herein, enteric diseases associated with coccidiosis are detected, particularly in livestock.

The experimental test of the method according to the present invention lasted a total of 45 days. The sample animals were bred in two identical separate rooms, both equipped with automatic control of ventilation.

A number of 120 commercial hybrid males of broiler chickens of 1 day of age were set up, divided into 2 boxes of size 3×2 m; so the animals were bred at a density of 30 kg/m$^2$ according to the management, regulated inter alia by the Council Directive "2007/43/EC minimum standards for the protection of chickens kept for meat production". As farming practices, for the first 8 days the chicks were bred under artificial mother at a T to 32° C.

The chicks in one of the room called "C3" were fed with a commercial feed for broilers with the addition of coccidiostat, as happens in the intensive farming of broiler chicken.

The chicks in the second room called "C4" were fed with feed free of coccidiostat as provided by the organic method of production of broiler chicken.

During the period of growth, the following parameters were detected: weekly individual weight of the animals; weight of the feed given daily; weekly feed residue to assess the food conversion index of the group (ICA); weekly count of oocysts present in the litter (5 points of pickup in the boxes) with Mc Master method.

The detection method of the present invention provides for the use of a sensor device of the "electronic nose" type according to the EN 13725 (UNI-CEN, 2003) standard, i.e. the collection of the samples was done using a "lung pump". This type of pump consists of a rigid frame provided with a waterproof cover and connected to a vacuum pump. The Nalophan bag is placed inside, a material expressly designated for measuring smell in the air (UNI-CEN, 2003), which fills with the sample air due to the vacuum created by the operation of the vacuum pump. Sampling was performed, in both rooms, throughout the lifecycle (45 days) with a weekly frequency in synchronization with the removal of the litter for the oocyst count.

The air samples were then analyzed in the laboratory by using an electronic nose made of a sampling unit, 10 hot metal oxide MOS sensors and data management and storage software.

The analysis carried out on samples of air collected inside the poultry shelter, identified as C3 where coccidiosis did not develop and C4 where coccidiosis occurred, provided an interesting differentiation between the two groups, in the evolution of the smelling track in 14 days represented in the Figure.

The graphs represent the signal detected by each of the hot MOS sensors described with reference to the sensor device 102.

The analysis of the main graph components shows that in the presence of coccidiosis (room C4), the air sampled in the environment is different from that collected from room C3. This is confirmed by the weekly count of oocysts contained in the animals' feces: room C4 day +14, number of oocysts/gram 37,300 vs total absence of oocysts/gram in group C3.

This analysis shows that the combination of the sensors selected can explain the variance between the two groups by 99.1% with a discriminating power (whose range is from 0 to 1) equal to a value of 0.9, indicating that the two samples belong to two different and separate classes. The sensitivity of the method was able to identify the "infected" group already with low oocyst charges (250 oocysts per gram, room C4 day D), two weeks in advance with respect to the emission peak of oocysts already commented.

In order to verify the correct operation of the detection system also in real cases, that is, commercial factory farms, air samples were taken in a factory farm of broiler chickens, using the same sampling system above. The air samples were collected in the center of the structure, of size 50×12 m, equipped with a cross ventilation system and hosting about 10,000 commercial hybrids of broiler chicken. Sampling was performed during the first, fourth and fifth week of the production cycle, since the outbreak of a sudden flu restricted access to breeding. Concurrently, litter samples were collected for the oocyst counts with the Mc Master method.

The data collected during the previous experimental test were used as reference values, dividing them into two clouds corresponding to infected animals (Group B) and uninfected animals (Group A) from coccidiosis, regardless of the number of oocysts. The division was done by linear discriminant analysis (LDA analysis), which was effective in distinguishing the two groups, as shown in FIG. 4.
an LDA normalization
there is a 6.18& variance in the ordinate and a 50.56% variance in the abscissa, for total variance of 56.738%.

The two air samples (FIG. 4, represented with x) collected in the factory farming in the first week were classified as not infected, while the other four (FIG. 4 represented with o for week 4 and with Δ for week 5) as being infected. The classification was confirmed by the subsequent oocyst counts, equal to 0 for the litter sample of the first week, fifty thousand for the sample of the fourth week and ten thousand for the sample of the fifth week.

These new data are stored by the system that will build increasingly dense and precise "clouds". In other words, the detection system is able to self-learn.

In perspective, the method is meant to be validated for all enteric diseases of bird species and other livestock (including mammals).

It is clear that many variations to the system exemplified are possible to the man skilled in the art.

For example, the detection system has been described in two exemplary embodiments, a distributed one where a remote processing server is used, and an "all in one" where the method is executed by a single device. The man skilled in the art can appreciate that what has been described only corresponds to illustrative, non-limiting possibilities, and that other variants of the detection system are easily conceivable considering the present description.

The method of the present invention may be advantageously implemented at least in part by a computer program which comprises encoding means for executing one or more steps of the method, when this program is run on a computer. Therefore, it is understood that the scope of protection extends to said computer program and moreover to computer-readable means which comprise a recorded message, said computer-readable means comprising program encoding means for executing one or more steps of the method when said program is run on a computer.

Embodiment variants of the non-limiting example described are possible without departing from the scope of protection of the present invention, comprising all the equivalent embodiments for a man skilled in the art.

The elements and the features shown in the different preferred embodiments may be combined without departing from the scope of protection of the present invention.

From the above description, the man skilled in the art is able to implement the object of the invention without introducing any further construction details.

The invention claimed is:

1. A detection system of enteric diseases in animals, comprising:
    a sensor device comprising suction for suctioning air from an environment with said animals, wherein said environment is a stable for pigs or a chicken coop, a sensor configured to determine information about type and concentration of a plurality of smelling molecules in said air and further configured to emit a signal representative of said information of smelling molecules;
    a transmission device configured to convey said signal representative of smelling molecules;
    a self-learning processing device configured to receive and process said signal representative of smelling molecules, detecting a risk of enteric diseases in said animals associated with said information about the type and concentration of said smelling molecules before said enteric diseases arise;
    a signaling device configured to report to a user said risk of enteric diseases in said animals;
    said processing device comprising a memory adapted to contain reference data by type and concentration of smelling molecules for enteric disease cases in animals, and a processor adapted to compare said information related to the type and concentration of the smelling molecules with the reference data, said processor being adapted to differentiate enteric diseases in animals by comparing a concentration of at least one type of smelling molecules with respect to reference values of the reference data.

2. The system according to claim 1, wherein said processing device is further adapted to store said information about the type and concentration of said smelling molecules by associating the smelling molecules with said reference data for subsequent analysis.

3. The system according to claim 1, wherein said sensor comprises a plurality of sensors, each being adapted to analyze at least a respective type of smelling molecule.

4. The system according to claim 3, wherein said plurality of sensors comprises metal oxide semiconductor (MOS) sensors for gases.

5. The system according to claim 1, wherein said transmission device comprises a bi-directional data exchange connection using an Internet connection.

6. The system according to claim 1, said processor being adapted to differentiate enteric diseases in animals by comparing a concentration of a plurality of types of smelling molecules with respect to reference values of the reference data.

7. A method of detecting enteric diseases in animals, comprising:
   suctioning air from an environment with said animals; wherein said environment is a stable for pigs or a chicken coop, determining with the sensor information about type and concentration of a plurality of smelling molecules in said air;
   detecting a risk of enteric diseases in said animals associated with said information about the type and concentration of said smelling molecules before said enteric diseases arise;
   reporting to a user said risk of enteric diseases in said animals;
   comparing said information about the type and concentration of said smelling molecules with reference data stored and concerning enteric disease cases in animals, wherein enteric diseases in animals are differentiated by comparing a concentration of at least one type of smelling molecules with respect to reference values of said reference data.

8. The method according to claim 7, wherein said information about the type and concentration of said smelling molecules are stored by associating the smelling molecules with said reference data for subsequent analysis.

9. The method according to claim 7, wherein a plurality of sensors are used, each being adapted to analyze at least a respective type of smelling molecule.

10. The method according to claim 9, wherein metal oxide semiconductor (MOS) sensors for gases are used.

11. The method according to claim 7, comprising exchanging data representative of smelling molecules between multiple electronic devices using an Internet connection.

12. The method according to claim 7, comprising detecting enteric diseases associated with coccidiosis in livestock.

13. A non-transitive computer program comprising a program coder adapted to execute the steps of claim 7, when said program is run on a computer.

14. A non-transitive computer-readable medium comprising a recorded program, said computer-readable medium comprising a program coder adapted to execute the steps of claim 7, when said program is run on a computer.

15. The method according to claim 7, wherein enteric diseases in animals are differentiated by comparing a concentration of a plurality of types of smelling molecules with respect to reference values of said reference data.

* * * * *